US011224489B2

(12) United States Patent
Ruiz Morales et al.

(10) Patent No.: US 11,224,489 B2
(45) Date of Patent: Jan. 18, 2022

(54) ROBOTIZED SURGERY SYSTEM WITH IMPROVED CONTROL

(71) Applicant: Asensus Surgical Italia S.R.L., Milan (IT)

(72) Inventors: Emilio Ruiz Morales, Milan (IT); Damien Brasset, Busnago (IT); Paolo Invernizzi, Milan (IT)

(73) Assignee: ASENSUS SURGICAL ITALIA, S.R.L., Milan (IT)

( * ) Notice: Subject to any disclaimer, the term of this patent is extended or adjusted under 35 U.S.C. 154(b) by 390 days.

(21) Appl. No.: 16/378,820

(22) Filed: Apr. 9, 2019

(65) Prior Publication Data

US 2019/0231456 A1    Aug. 1, 2019

Related U.S. Application Data

(63) Continuation of application No. 15/149,512, filed on May 9, 2016, now Pat. No. 10,251,713, which is a
(Continued)

(30) Foreign Application Priority Data

Apr. 7, 2010    (IT) .......................... MI2010A000579

(51) Int. Cl.
*A61B 17/00* (2006.01)
*A61B 3/113* (2006.01)
(Continued)

(52) U.S. Cl.
CPC .............. *A61B 34/30* (2016.02); *A61B 17/00* (2013.01); *G06F 3/013* (2013.01); *G06F 3/0482* (2013.01);
(Continued)

(58) Field of Classification Search
CPC ......... A61B 34/30; A61B 17/00; A61B 34/37; A61B 90/361; A61B 3/113; A61B 5/11;
(Continued)

(56) References Cited

U.S. PATENT DOCUMENTS 6,847,336 B1 *   1/2005   Lemelson ............. G16H 20/40
                                                                 345/8
10,152,141 B1 *  12/2018  Lohse .................. G06F 3/0308
(Continued)

FOREIGN PATENT DOCUMENTS

DE         10226539 A1    1/2004
DE      102006011233 A1    9/2007
(Continued)

OTHER PUBLICATIONS

S. M. Ali et al. "Eye gaze tracking for endoscopic camera positioning: an application of a hardware/software interface developed to automate Aesop." Studies in Health Technology and Informatics. 2008, pp. 4-7.
(Continued)

*Primary Examiner* — Robert T Nguyen (57) ABSTRACT

A robotized surgery system comprises at least one robot arm which acts under the control of a control console intended for the surgeon. The console comprises an eye tracking system for detecting the direction of the surgeon's gaze and for entering commands depending on the directions of the gaze detected. The console comprises advantageously a screen with at least one zone for viewing the operating field and, among the commands which can be performed depending on the gaze directions.

17 Claims, 4 Drawing Sheets

Related U.S. Application Data continuation of application No. 13/639,809, filed as application No. PCT/IB2011/051397 on Apr. 1, 2011, now Pat. No. 9,360,934.

(51) Int. Cl.

| | |
|---|---|
| *A61B 34/37* | (2016.01) |
| *A61B 90/00* | (2016.01) |
| *G06F 3/01* | (2006.01) |
| *G06F 3/0482* | (2013.01) |
| *A61B 34/30* | (2016.01) |
| *G06F 3/0484* | (2013.01) |
| *G06K 9/00* | (2006.01) |
| *A61B 5/11* | (2006.01) |

(52) U.S. Cl.
CPC ...... *G06F 3/04842* (2013.01); *G06F 3/04847* (2013.01); *G06K 9/00604* (2013.01); *A61B 3/113* (2013.01); *A61B 5/11* (2013.01); *A61B 34/37* (2016.02); *A61B 90/361* (2016.02); *A61B 2017/00216* (2013.01)

(58) Field of Classification Search
CPC .......... A61B 2017/00216; A61B 34/00; A61B 90/30; A61B 34/25; A61B 2017/00199; A61B 34/74; G06F 3/0482; G06F 3/04842; G06F 3/04847; G06F 3/013; G06K 9/00604
See application file for complete search history.

(56) References Cited

U.S. PATENT DOCUMENTS

| | | | |
|---|---|---|---|
| 11,083,601 B1* | 8/2021 | Leonard | A61F 2/588 |
| 11,087,271 B1* | 8/2021 | Guan | G06Q 10/087 |
| 2006/0074307 A1 | 4/2006 | Igarashi et al. | |
| 2006/0109237 A1 | 5/2006 | Morita et al. | |
| 2007/0083098 A1 | 4/2007 | Stern et al. | |
| 2007/0279591 A1 | 12/2007 | Wezowski et al. | |
| 2008/0027591 A1 | 1/2008 | Lenser et al. | |
| 2008/0253519 A1* | 10/2008 | Bonfiglio | G16H 40/63 |
| | | | 378/65 |
| 2009/0248036 A1* | 10/2009 | Hoffman | A61B 1/00149 |
| | | | 606/130 |
| 2009/0307601 A1* | 12/2009 | Kumhyr | G06F 21/84 |
| | | | 715/741 |
| 2010/0205667 A1 | 8/2010 | Anderson et al. | |
| 2011/0118748 A1 | 5/2011 | Itkowitz | |
| 2012/0069166 A1* | 3/2012 | Kunz | G06F 3/013 |
| | | | 348/65 |
| 2012/0154564 A1 | 6/2012 | Hoffman et al. | |
| 2013/0096575 A1 | 4/2013 | Olston | |
| 2014/0024889 A1 | 1/2014 | Xiaoli | |
| 2014/0049452 A1 | 2/2014 | Maltz | |
| 2014/0055578 A1 | 2/2014 | Wu et al. | |
| 2014/0171964 A1 | 6/2014 | Yang et al. | |
| 2014/0275760 A1 | 9/2014 | Lee et al. | |

FOREIGN PATENT DOCUMENTS

| | | |
|---|---|---|
| DE | 102009010263 A1 | 9/2010 |
| WO | 2004029786 A1 | 4/2004 |
| WO | 2006087689 A2 | 8/2006 |
| WO | 2007088208 A1 | 8/2007 |
| WO | 2008088206 A2 | 8/2007 |
| WO | 2008049898 A1 | 5/2008 |
| WO | 2010021447 A1 | 2/2010 |
| WO | 2011125007 A1 | 10/2011 |

OTHER PUBLICATIONS

Chung, A. J. et al., "Extraction of Visuals Features with Eye Tracking for Saliency Driven 2D/3D Registration," Image and Vision Computing, Oct. 1, 2005, vol. 23, No. 11, pp. 999-1008.

Italian Search Report, dated Oct. 21, 2010, Munich, IO 14151, IT MI20100579, 11 pages.

Noonan, D. P. et al., "Gaze Contingent Articulated Robot Control for Robot Assisted Minimally Invasive Surgery," Intelligent Robots and Systems, 2008 IEEE/RSJ International Conference on Intelligent Robots and Systems, Acropolis Convention Center, Nice, France, Sep. 22-26, 2008, 6 pages.

International Search Report, dated Aug. 19, 2011, International Application No. PCT/IL2011/051397, International Filing Date: Apr. 1, 2011, Applicant: SOFAR SPA, 10 pages.

* cited by examiner

ROBOTIZED SURGERY SYSTEM WITH IMPROVED CONTROL

The present invention relates to a robotized surgery system, in particular for mini-invasive operations, such as endoscopies.

In the prior art robotized systems for performing surgical operations, in particular laparoscopic operations, have been proposed. These robotized systems comprise one or more robot arms which are controlled by a surgeon via a special console. Said console generally comprises a television screen, on which the pictures of the operating field (usually recorded by means of an endoscopic telecamera) are shown, and suitable manipulators by means of which the surgeon performs the movements of the robot arms. The manipulators may be of the "reactive" type such that the surgeon is also able to feel with his/her hands the forces exerted by the robotized surgical instruments on the patient's tissues.

Usually, one of the robot arms moves the telecamera so that the surgeon is able to vary its viewing angle during the operation, while one or more robot arms move(s) the operating instruments (forceps, scissors, scalpels, aspirators, etc.) with which the surgeon performs the intended operation.

It is somewhat complicated for the surgeon to control the system owing to the number of controls available and the number of operating parameters which the surgeon must oversee. In addition to the movement of the robot arms, the surgeon must also operate the surgical implements mounted on the arms (for example, control opening and closing of the forceps or scissors) and control the telecamera lens so as to have closer or more distant pictures of the operating field as required in any one moment.

Often the surgeon, while looking at the picture shown by the telecamera, must simultaneously operate two robot arms with the surgical implements, such that both his/her hands are occupied controlling the corresponding manipulators.

This prevents the surgeon from being able to use other system functions, unless he/she removes one of his/her hands from the surgical implement controls.

Systems have also been proposed where certain functions can be activated by using pedals or additional control devices provided on the manipulators so that they can be operated with a finger without having to let go of the manipulator itself. All these systems, however, are often not intuitive and, in any case, distract the attention of the surgeon when performing a precise manoeuvre with the surgical manipulators.

A further problem is that the surgeon's attention, for one reason or another (for example, in order to perform further functions or view the operating parameters shown on the console or on other instruments outside of the operating field), may be distracted from the picture of the operating field. In these conditions, the surgeon may not notice incorrect or dangerous movements of the robotized surgical instruments, which may also be involuntarily performed by him/her while gripping the manipulators.

In order to avoid such situations it has been proposed using a pedal which the surgeon must operate in order to activate/deactivate movement of the robots, so as to be able to deactivate the movement before removing his/her hands from the manipulators and directing his/her attention away from the operating field. Timely operation of this pedal, however, depends on the surgeon.

The main object of the present invention is to provide a robotized surgery system and a control method which allow better and safer control by the surgeon, thus ensuring, among other things, better operating safety of the system.

In view of this object, the idea which has arisen according to the invention is to provide a robotized surgery system comprising at least one robot arm which acts under the control of a control system intended for the surgeon, characterized in that the console comprises an eye tracking system for detecting the direction of the surgeon's gaze and for entering commands depending on the gaze directions detected.

A further idea according to the invention is to provide a method for controlling a robotized surgery system comprising at least one robot arm which acts under the control of a control console intended for the surgeon, in which the direction of the surgeon's gaze is detected and functions of the surgery system are controlled depending on the gaze direction detected.

In order to illustrate more clearly the innovative principles of the present invention and its advantages compared to the prior art, an example of embodiment applying these principles will be described below, with the aid of the accompanying drawings. In the drawings.

Figure 1:
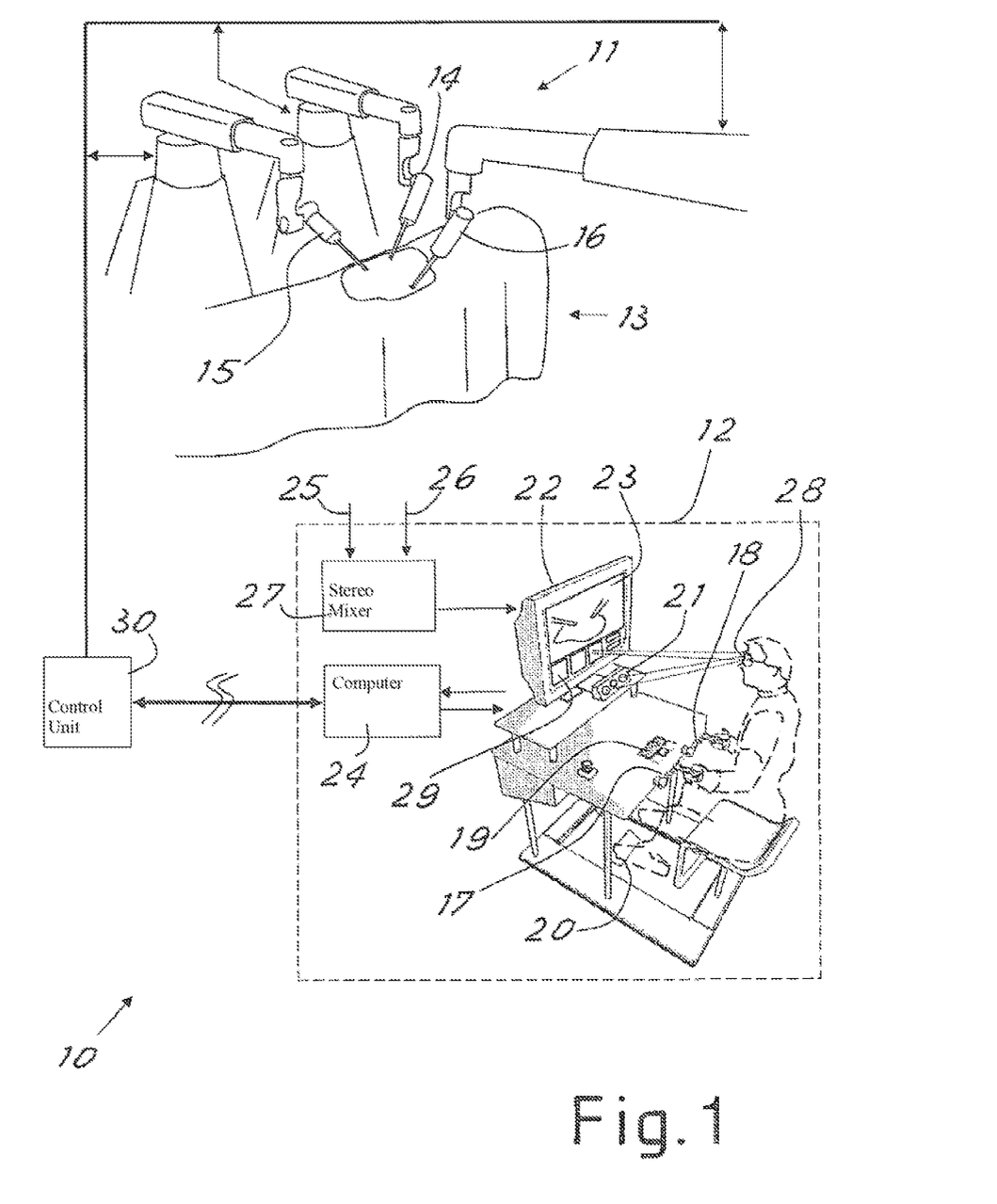
FIG. 1 shows a schematic view of a surgery system according to the invention.

With reference to the figures, FIG. 1 shows in schematic form a robotized surgery system, denoted generally by 10, provided according to the invention.

The system 10 comprises at least one robot arm 11 which acts under the control of a control console 12 managed by the surgeon who is for example sat in a comfortable working position.

The console may also be mounted on wheels so that it can be easily displaced.

The robot arm will be of the substantially known type suitable for the specific use. In the system 10 shown here the robot arms are three in number, although a different number may be easily used.

The robot arm (or each robot arm) terminates in a wrist piece which is able to support and operate a surgical instrument for use on a patient 13. This instrument will usually be a known instrument for endoscopic, and in particular laparoscopic, operations. One of the instruments is advantageously a telecamera 14 which records the operating field (in this particular case, the patient's interior), while the other instruments may be suitable known surgical tools 15, 16 (forceps, aspirators, scalpels, etc.). The robot arms, the instruments and the actuators for manoeuvring these instruments will not be described and illustrated further here, since they are known and may be easily imagined by the person skilled in the art. The surgical operations which are possible with the system and the methods for performing them are also not further described here, since they may be easily imagined by the person skilled in the art.

The robot arms are operated by a suitable known electronic control unit 30 so as to perform the movements entered via the console 12. The unit 30 will receive the high-level movement commands (for example, desired position and inclination of the tool supported by the robot) and will execute them, converting them into the corresponding sequences of signals to be sent to the individual motors of the robot arm articulations. The robot arms may also be provided with known force sensors, used both by the unit 30 to prevent damage due to collision of the arm with objects in the working space, and in order to provide suitable feedback to the operator at the console, as will be clarified below. The connections between the console and the unit for controlling the robots may be advantageously of the optical fibre type, in order to reduce the possibility of interference with the signals transmitted.

Suitable robot arms and control systems are, for example, described in WO2007/088208, WO2008/049898 and WO2007/088206.

In order to perform the movements of the surgical instruments, the console may advantageously comprise a pair of known manipulators 17, 18 which can be gripped by the surgeon and the movements of which are suitably reproduced by the surgical instruments by means of movement of the robot arms 11. Advantageously, the manipulators may be of the known "reactive" type (i.e. with a tactile interface which provides a weighted movement and tactile sensing) such that the surgeon is also able to feel on the manipulators the forces exerted by the robotized surgical instruments on the patient's tissues. Suitable tactile interfaces are well-known in the sector of robotized endoscopic surgery.

Usually, each manipulator will operate a robot arm. Advantageously, in the case of more than two arms, a control will be provided on the console so as to be able to assign, as required, each manipulator to a desired robot arm, as will be explained further below. A keyboard 19 and other command input devices, for example also comprising a pedal device 20, may also be envisaged.

The device 20 may comprise one or more pedals for activating, for example, the supply of power for monopolar and bipolar instruments, the irrigation and aspiration functions, if envisaged for a specific instrument, etc.

The console 12 also comprises an eye movement tracking system 21 or so-called "eye tracker" for detecting the direction of the surgeon's gaze towards the console and for controlling the surgical system also depending on the gaze directions detected. In this way, the surgeon may control functions of the system by means of movement of the eyes.

Advantageously, the console comprises a video screen 22 with at least one zone 23 for showing a view of the operating field. This view is provided by the telecamera 14 which may be supplemented (for example so as to provide the surgeon with additional information and/or improve his/her understanding of the operating field) with artificial pictures generated by a computerized system 24, known per se, for managing the console, which will be further described below.

As will become clear below, the computerized system 24 generates and manages a human machine interface (HMI) which allows the surgeon to interact with the surgical system.

For conventional two-dimensional viewing, the picture supplied by the endoscope may be directly viewed on the screen 22.

Advantageously, however, a three-dimensional system for viewing the operating field may be envisaged. In this case, the telecamera 14 may be of a known stereoscopic type which provides suitable signals 25, 26 representing two different "right-hand" and "left-hand" pictures which are recorded spatially offset. The signals 25, 26 are processed by an electronic device 27 so that the 3D picture may be shown to the surgeon by means of a stereoscopic viewing system.

From among the various known stereoscopic viewing systems a polarized filter system has been found to be particularly advantageous; in this system the electronic device 27 comprises a known stereo mixer which alternates lines of the right-hand and left-hand pictures received from the telecamera so as to display them interlaced in the viewing area 23 of the screen. Alternate odd and even horizontal lines of the picture on the screen thus represent alternately lines of the right-hand and left-hand pictures recorded by the telecamera.

A known filter provided with two different polarization modes for the even interlaced lines and the odd interlaced lines is provided in the area 23 for viewing this interlaced picture. In order to view the picture, the surgeon wears glasses 28 with the two lenses polarized in a manner corresponding to the two polarization modes of the filter on the screen, so as to direct towards the right eye only the lines of the picture belonging to the original right-hand picture recorded by the telecamera, while the left-hand eye receives only the lines of the picture belonging to the original left-hand picture recorded by the telecamera.

It is thus possible to show the surgeon the desired 3D picture of the operating field.

If desired, using a similar procedure, artificial stereoscopic pictures produced by the computerized system 24 may also be shown in 3D form.

In any case, by means of the tracking system 21 it is possible to detect the direction of the surgeon's gaze towards the screen 22 and define which zone of the screen he/she is looking at or not looking at. Using a 3D viewing system with polarized glasses there is no interference with the tracking system. Moreover, glasses with polarized lenses for 3D viewing can be easily designed so as to be compatible with the normal eyeglasses.

It has been found to be particularly advantageous for the tracking system to send a command which disables the movement of the robot arms when a direction of the gaze which falls outside of the screen, or at least outside of the screen zone which reproduces the operating field, is detected. See FIG. 4C. In this way, a safety system preventing movements of the arms without direct supervision of the surgeon is provided.

A so-called "dead man's" function is thus obtained for activating the robot and keeping it activated while the user is looking at the screen.

Advantageously, for additional safety, a further control means may be provided (for example a pushbutton 31 on a handgrip or a pedal device 20) where it is required to give a dual consent for enabling the movement commands so that, in order to reactivate the movement, the surgeon must look at the picture on the screen and also give a manual consent command, while the movement may be interrupted by simply looking away from the picture.

Advantageously, the screen 22 shows, in addition to the view from the endoscope, also at least part of the human machine interface. The computerized system 24 which provides the interface shows on a screen selection areas 29 associated with system commands. Advantageously, the selection areas may be arranged on the same screen 22 which shows the view of the operating field. For example, these selection areas may be arranged in the bottom part of the screen, underneath the area 23 for viewing the operating field. The tracking system estimates the direction of the surgeon's gaze and performs selection of the commands associated with a selection area when it detects a gaze direction which falls within this area.

The commands associated with the various selection areas may be of any type considered to be useful. For example, these commands may be chosen from among those which are frequently used when performing a robotized surgery operation.

It has been found to be particularly advantageous (in particular when the console comprises two operating manipulators and more than two robot arms) if the commands associated with the selection areas comprise the commands for assigning the manipulators to the robot arms.

The surgeon may thus alternate control of the various robot arms on the two manipulators, without letting go of the manipulators, but instead simply looking at the corresponding selection areas. For example, the surgeon may temporarily switch over to control of the arm with the telecamera, in order to modify the view of the operating field, and then rapidly return to control of the robot arm with which he/she was operating.

For additional safety, the console may advantageously comprise a device for inputting a special command confirming execution of the command associated with the selection area looked at. This device may advantageously be a pushbutton 31 which is arranged on one or both the manipulators, so as to be pressed, for example, using the thumb of the hand gripping the manipulator. It is thus possible to confirm easily the actions activated by the eyes via the eye tracking system, for example in order to select a robot to be associated with the manipulator, open/close the surgical instruments and modify the settings of the robot which is being operated. Another use of the pushbutton may also be that of controlling the degree of freedom of a twisting movement on the instrument (if available).

It is also possible to envisage advantageously that the procedure for assigning a robot may be performed by visually selecting the picture of the new robot which is to be assigned, confirming the selection by means of the pushbutton and then dragging the picture selected into the position where the picture of the robot currently assigned to the right-hand grip or left-hand grip is shown. Dragging is performed by keeping the pushbutton pressed and directing one's gaze towards the robot position. In order to end the dragging operation, the pushbutton must be released while keeping one's gaze focused on the previously indicated zone.

The eye tracking system may be one of the many types which are known per se. However, an eye tracking system which has been found to be particularly advantageous is one comprising at least one telecamera for recording the picture of at least the surgeon's eyes and means for calculating the direction of the gaze depending on the picture taken.

Figure 2:
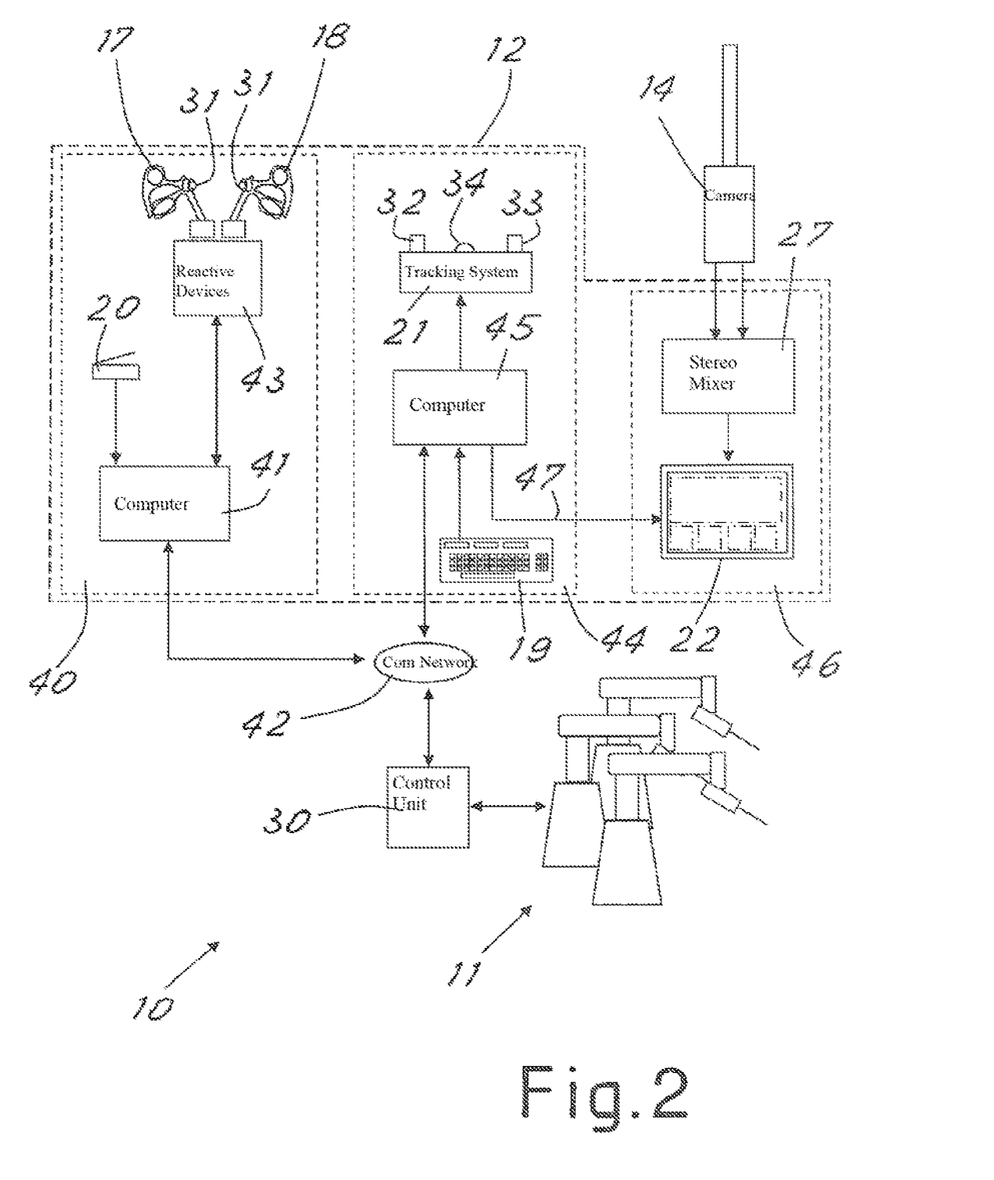
FIG. 2 shows block diagram of the system according to the invention.

In particular, as shown schematically in FIG. 2, the tracking system 21 may comprise two telecameras 32, 33 which are arranged alongside each other at a suitable distance so as to record two spatially offset pictures of the surgeon's eyes. The calculation means (for example comprising a suitably programmed microprocessor) present in the tracking system 21 may thus perform a triangulation of the gaze direction depending on the comparison of the two recorded pictures. Again advantageously, the tracking system may also comprise an infrared light source 34 for infrared illumination of the eyes, this facilitating detection thereof in the picture recorded. Advantageously the eye tracking system may be integrated with the monitor so that if the latter is moved, the eye tracker may continue to operate correctly.

Still with reference to FIG. 2, a block diagram of a possible advantageous embodiment of the console is schematically shown. In this embodiment, the system is divided up for the sake of clarity into three main functional blocks or groups.

The first block, indicated by 40, comprises the components which are involved directly in the movement of the robot arms. The block 40 contains a first industrial computer 41, known per se, provided with a real-time operating system (for example, RT-LINUX) for carrying out in a given predefinable time the commands associated with control of the robots. The computer 41 is connected to the robot control unit (or units) 30 via the communications network 42. The computer 41 receives the movement commands from the manipulators 17 and 18, sending them to the robots and emitting signals for operation of the reactive devices 43 of the manipulators for tactile feedback. Those manual controls which require an immediate system response, such as the pedals 20, if used to send, among other things, commands for stopping the movement of the robot, are also advantageously connected to the computer 41.

The second functional block, which is indicated by 44, comprises a second industrial computer 45 which produces and controls the human machine interface (HMI) which does not require strictly real-time operation. The eye tracking system 21, the keyboard 19 (where necessary) and the other interface controls are connected to this second computer. The computer 45 also produces the artificial video pictures to be reproduced on the screen 22 (for example the visual control areas 31) and may control any functions for varying the enlargement of the operating field picture.

The computers 41 and 45 form the computerized system 24 for controlling the console.

The computers 41 and 45 and the robot control unit 30 may communicate with each via the network 42. The HMI application managed by the computer 45 thus allows the robots to be assigned to the manipulators, as well as display of the data relating to each robot, such as the instruments currently mounted, the movement state, the feedback state, the position of rotational fulcrums of the instruments inserted inside the patient's body, the robot condition, the robot connection state, any emergency conditions, etc.

The third functional block, indicated by 46, deals with reproduction of the pictures on the screen, providing for example the PiP (Picture-in-Picture) function using the signal supplied by the telecamera 14 recording the operating field and the picture signal 47 produced in order to display the HMI interface. The third block also comprises the stereo mixer 27 for three-dimensional viewing.

Advantageously, for the PiP function the monitor 22 is designed with two separate inputs. The main source is displayed in full screen mode by means, for example, of a DVI connection, while at the same time another video input (for example a VGA connection) is displayed as an inset window. The main source (full screen) consists of the 2-dimensional or 3-dimensional view of the endoscope which is received from the endoscope system. The second source comes from the computer 45 which produces the human machine interface (HMI).

During calibration of the eye tracking system 21, the full-screen view may also be switched dynamically (for example, by means of a serial command sent from the HMI application to the monitor) to the video signal produced by the computer 45.

Advantageously, the console may also comprise a system for detecting the distance between screen and surgeon's eyes in order to vary enlargement of the picture of the operating field shown on the screen depending on a variation in the distance detected.

Thus, the surgeon may intuitively perform enlargement of the picture by simply moving his/her face towards the screen and, vice versa, increase the viewing area of the operating field, thus reducing enlargement, by moving his/her face away from the screen.

The distance detection system may be achieved in various ways, known per se, for example using telemetric ultrasound measurement devices.

Advantageously, however, the eye tracking system 21 may be used, owing to the stereoscopic recording system which allows calculation, by means of triangulation, of the distance of the surgeon's face. This, together with the associated eye detection function of the eye tracking system, allows an accurate real measurement of the distance of the surgeon's viewpoint from the screen to be performed.

In addition to an enlargement, the system may also produce a displacement of picture, for example so as to centre the picture, or displace the picture, by means of the gaze, to the right, to the left, upwards or downwards.

Figure 3A:
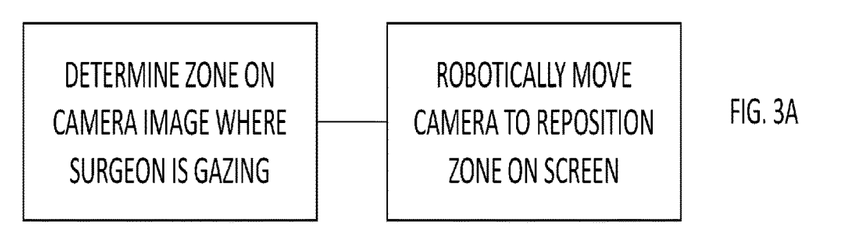
FIGS. 3A and 3B show the steps of a method according to the invention.
Figure 3B:
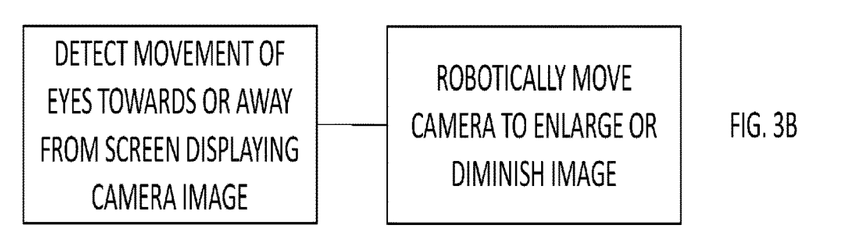
Figure 4A:
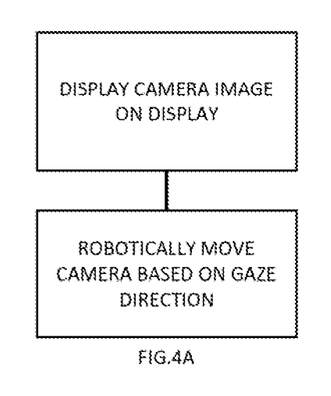
FIGS. 4A, 4B and 4C show steps of methods performed using the disclosed system.
Figure 4B:
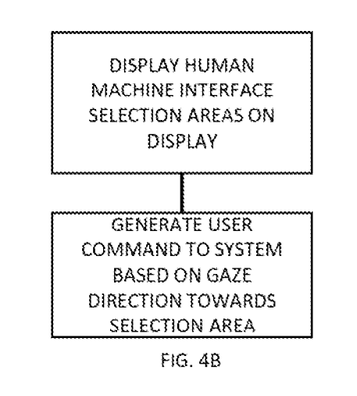
Figure 4C:
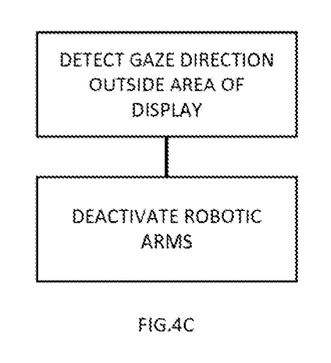

When the operating field is recorded by a telecamera, preferably an endoscopic telecamera, mounted on one of the robot arms, it has been found to be advantageous for the gaze detection tracking system to allow also control of the movement of this telecamera in the manner depicted in FIGS. 4A 3A and 3B. When this function is enabled (for example, by entering, by means of visual selection of a suitable area 29, the associated activation command), the movement of the eyes over the picture of the operating field causes the movement of the robot arm so as to displace, and advantageously centre on the screen, the zone focused on. Control of the actual movement of the telecamera may also be performed only following pressing of a confirmation pedal or pushbutton, as already described above. In this way, the surgeon is free to move his/her eyes over the picture without displacement of the viewing frame unless the confirmation pedal or pushbutton is simultaneously pressed. If the movement and enlargement functions described above are combined, the system becomes very easy to control, the movements of the gaze displacing the viewing frame on the screen, while the movement of the eyes towards or away from the screen enlarges or diminishes the picture shown.

When three-dimensional viewing of the operating field is used, the distance detection system may also be used to signal to the surgeon when he/she is within the optimum distance range from the screen.

In fact, usually three-dimensional systems have an optimum distance interval from the screen where the three-dimensional effect is best.

Moreover, the combination of 3D and eye tracking system imposes certain constraints with regard to the position and the distance from the screen, said constraints depending on the position of the surgeon, the tracker and the viewing device.

The HMI application of the console may be set so as to indicate to the surgeon, by means of various known acoustic and/or optical systems, when he/she is situated in the optimum position with respect to the screen. Moreover, it is also possible to provide a function which indicates whether the distance with respect to the eye tracker is adequate. When the 3D and eye tracker are used together, the appropriate working space may be the same for both of them and the same indicator may perform both functions.

The working area of the eye tracker 21 will generally be chosen so as to be much greater than that for optimum viewing of the three-dimensional picture. For example, an operating range of the tracker lying between 40 and 75 cm has been found to be advantageous, with the possibility of tracking the eyes within a vertical angle of +30° and −10°. The optimum 3D view is obtained at 60-70 cm from the screen (in this range, the information will be perfectly differentiated between right eye and left eye) and therefore falls well within the operating zone of the tracker. However, it will still be possible to view in 3D outside of this range, provided that the surgeon respects the vertical constraint. Beyond the top end and bottom end of the screen, the 3D is lost. At this point it is clear how the predefined objects have been achieved. With the control system and method described it is possible to control the robot arms with tactile sensing, display the view provided by the endoscope in two or three dimensions, together with the HMI application, and activate certain functions using an eye movement tracker. Owing to the use of the eye tracking system, various interesting control possibilities exist. Firstly, among the various functions associated with the eye tracking system, there is that of being able to stop safely the movement of the robot arms if the surgeon is not looking at the picture of the operating field, with movement of the robot arm which is prevented or allowed automatically when the gaze direction detected does not fall or falls within the predetermined zone of the screen.

Moreover, the HMI application is intuitive and easy to use since it may be controlled by the surgeon's gaze (together with or without an activation confirmation device). The main advantages are that the surgeon is able to use his/her eyes in order to select and assign the robot arms to the manipulators without removing his/her hands from the manipulators.

Obviously, the above description of an embodiment applying the innovative principles of the present invention is provided by way of example of these innovative principles and must therefore not be regarded as limiting the scope of the rights claimed herein. For example, the console forms a remote operation surgical workstation for the robotized system which may be in the same room or at a distance, also using a connection via geographic networks or the like. The main control console is in fact a remote control device which also allows a patient to be operated on outside of the operating theatre and in any location, as long as the communications time delays are limited.

The remote surgery system will be suitable for any type of laparoscopic or similar operation. Obviously, here the term "surgeon" is understood as meaning any person who controls the robot system by means of the console.

It must be noted that, as can now be easily imagined by the person skilled in the art, the system according to the invention is modular and may for example be configured to use a greater number of robots (for example up to five robots) and also one or two control consoles.

We claim:

1. A method for controlling a surgical system comprising:
providing first and second robotic arms, each carrying a surgical instrument, and a third robotic arm carrying an endoscopic camera;
causing movement of the first and second robotic arms to move the surgical instruments by manipulating a pair of hand manipulators at a surgeon console;
displaying on a display at the surgeon console an image from the endoscopic camera and a human machine interface comprising a plurality of computer-generated selection areas, each selection area corresponding to a user command;
using an eye tracking system to generate signals based on the estimated direction of a user's gaze towards the display, and operating the system in a first mode in which movement of the third robotic arm is commanded based on signals from the eye tracking system corresponding to an estimated direction of the user's gaze towards the image, and in response to user actuation of an auxiliary input on at least one of the hand manipulators, operating the system in a second mode in which a user command to the system is generated based on signals from the eye tracking system corresponding to an estimated direction of the user's gaze towards a selection area.

2. The method of claim 1, further including operating the system in a third mode in which the first, second and third robotic arms are deactivated in response to signals from the eye tracking system indicating that the estimated direction of the user's gaze is outside an area of the display.

3. The method of claim 1, further including operating the system in a third mode in which the third robotic arm moves the camera in response to the signals from the eye tracking system.

4. The method of claim 3, wherein in the third mode the third robotic arm moves the camera based on signals from the eye tracking system corresponding to an estimated direction of the user's gaze towards the image.

5. A method for controlling a surgical system comprising:
providing first and second robotic arms, each carrying a surgical instrument, and a third robotic arm carrying an endoscopic camera;
causing movement of the first and second robotic arms to move the surgical instruments by manipulating a pair of hand manipulators at a surgeon console;
displaying on a display at the surgeon console an image from the endoscopic camera and a human machine interface comprising a plurality of computer-generated selection areas, each selection area corresponding to a user command;
using an eye tracking system to generate signals based on the estimated direction of a user's gaze towards the display, and
operating the system in a first mode in which movement of the third robotic arm is commanded based on signals from the eye tracking system corresponding to an estimated direction of the user's gaze towards the image, and
operating the system in a second mode in which a user command to the system is generated based on signals from the eye tracking system corresponding to an estimated direction of the user's gaze towards a selection area, wherein in the second mode, each of the manipulators is assigned to a corresponding one of the first and second robotic arms based on the signals.

6. The method of claim 5, further including operating the system in a third mode in which the system is responsive to the signals from the eye tracking system to cause the third robotic arm to move the camera.

7. The surgical system of claim 6, wherein in the third mode the third robotic arm moves the camera based on signals from the eye tracking system corresponding to an estimated direction of the user's gaze towards the image.

8. A surgical system comprising:
first and second robotic arms, each carrying a surgical instrument;
a third robotic arm, the third robotic arm carrying an endoscopic camera,
a surgeon console including
a display displaying an image from the endoscopic camera and further displaying a human machine interface comprising a plurality of computer-generated selection areas, each selection area corresponding to a user command;
an eye tracking system, and
a pair of manipulators, each manipulators moveable by a user's hands to generate movement command signals for a corresponding one of the first and second robotic arms, at least one of the manipulators including a manually-actuatable auxiliary input;
the system operable in
a first mode in which movement of the third robotic arm is commanded based on signals from the eye tracking system corresponding to an estimated direction of the user's gaze towards the image, and
a second mode in which a user command to the system is generated in response to user actuation of the auxiliary input, said user command based on signals from the eye tracking system corresponding to an estimated direction of the user's gaze towards a selection area.

9. The system of claim 8, wherein the system is further operable in a third mode of operation in which the first, second and third robotic arms are deactivated in response to signals from the eye tracking system indicating that the estimated direction of the user's gaze is outside an area of the display.

10. The system of claim 8, wherein the system is further operable in a third mode in which the system is responsive to the signals from the eye tracking system to cause the third robotic arm to move the camera.

11. The surgical system of claim 10, wherein in the third mode of operation the third robotic arm moves the camera based on signals from the eye tracking system corresponding to an estimated direction of the user's gaze towards the image.

12. A surgical system comprising:
first and second robotic arms, each carrying a surgical instrument;
a third robotic arm, the third robotic arm carrying an endoscopic camera,
a surgeon console including
a display displaying an image from the endoscopic camera and further displaying a human machine interface comprising a plurality of computer-generated selection areas, each selection area corresponding to a user command;
an eye tracking system for generating signals based on the estimated direction of a user's gaze towards the display, and
a pair of manipulators, each manipulators moveable by a user's hands to generate movement command signals for a corresponding one of the first and second robotic arms;
the system operable in
a first mode in which movement of the third robotic arm is commanded based on the signals from the eye tracking system corresponding to an estimated direction of the user's gaze towards the image, and
a second mode in which a user command to the system is generated based on signals from the eye tracking system corresponding to an estimated direction of the user's gaze towards a selection area, in which, wherein, in the second mode of operation, assignment of each of the manipulators to a corresponding one of the first and second robotic arms is performed based on the signals.

13. The system of claim 12, wherein the system is further operable in a third mode in which the system is responsive to the signals from the eye tracking system to cause the third robotic arm to move the camera.

14. The surgical system of claim 13, wherein in the third mode of operation the third robotic arm moves the camera based on signals from the eye tracking system corresponding to an estimated direction of the user's gaze towards the image.

15. A surgical system comprising:
- a first robotic arm carrying a surgical instrument;
- a second robotic arm carrying an endoscopic camera,
- a surgeon console including
  - a screen displaying an image from the endoscopic camera and further displaying a human machine interface comprising a plurality of computer-generated selection areas, each selection area corresponding to a user command to the system;
  - an eye tracking system for generating signals based on the detected direction of a user's gaze towards the console, and
  - a manipulator moveable by a user's hand to generate movement command signals for the first robotic arm;
- the system causing movement of the first robotic arm in response to movement of the manipulator, and performing a selection of commands associated with the selection area when the estimated direction of the user's gaze falls within said one area and the user actuates an input on the manipulator.

16. The surgical system of claim 15, the system further causing movement of the second robotic arm based on signals from the eye tracking system corresponding to an estimated direction of the user's gaze towards the image.

17. The surgical system of claim 16, wherein movement of the second robotic arm is caused based on signals from the eye tracking system only in the presence of user actuation of an input on the hand manipulator.

* * * * *